(12) United States Patent
Röhr

(10) Patent No.: US 8,883,205 B2
(45) Date of Patent: Nov. 11, 2014

(54) MICROTABLET-BASED PHARMACEUTICAL PREPARATION

(75) Inventor: Wolfgang Röhr, Hamburg (DE)

(73) Assignee: Biogenerics Pharma GmbH, Hamburg (DE)

( * ) Notice: Subject to any disclaimer, the term of this patent is extended or adjusted under 35 U.S.C. 154(b) by 573 days.

(21) Appl. No.: 12/223,833

(22) PCT Filed: Feb. 9, 2007

(86) PCT No.: PCT/DE2007/000415
§ 371 (c)(1),
(2), (4) Date: Dec. 22, 2008

(87) PCT Pub. No.: WO2007/090393
PCT Pub. Date: Aug. 16, 2007

(65) Prior Publication Data
US 2009/0175936 A1    Jul. 9, 2009

(30) Foreign Application Priority Data

Feb. 10, 2006    (DE) .................... 10 2006 006 532

(51) Int. Cl.
*A61K 9/20*    (2006.01)

(52) U.S. Cl.
CPC .................. *A61K 9/2072* (2013.01)
USPC ....................................... 424/464

(58) Field of Classification Search
USPC ............... 424/464, 480, 468; 514/571
See application file for complete search history.

(56) References Cited

U.S. PATENT DOCUMENTS

| | | | |
|---|---|---|---|
| 4,797,287 A * | 1/1989 | Pich et al. ............. | 424/464 |
| 4,828,843 A * | 5/1989 | Pich et al. ............. | 424/480 |
| 5,681,588 A | 10/1997 | Kolter et al. | |
| 5,945,124 A | 8/1999 | Sachs et al. | |
| 6,063,313 A * | 5/2000 | Briskin et al. ......... | 264/15 |
| 6,068,856 A | 5/2000 | Sachs et al. | |
| 6,274,173 B1 | 8/2001 | Sachs et al. | |
| 6,399,104 B1 * | 6/2002 | Creekmore et al. .... | 424/490 |
| 6,419,959 B1 | 7/2002 | Walter et al. | |
| 6,811,054 B1 | 11/2004 | Moest et al. | |
| 7,276,253 B2 | 10/2007 | Heese et al. | |
| 2002/0054913 A1 | 5/2002 | Heese et al. | |
| 2002/0156133 A1 | 10/2002 | Bartholomaeus et al. | |
| 2003/0124061 A1 | 7/2003 | Roberts | |
| 2004/0115267 A1 | 6/2004 | Bartholomaus et al. | |
| 2004/0214860 A1 | 10/2004 | Charous | |
| 2004/0220220 A1 | 11/2004 | Charous | |
| 2005/0058704 A1 | 3/2005 | Schneider et al. | |
| 2005/0064035 A1 | 3/2005 | Heese et al. | |
| 2005/0203186 A1 * | 9/2005 | Kraass ................. | 514/571 |
| 2005/0249947 A1 | 11/2005 | Wittmann | |
| 2005/0282784 A1 | 12/2005 | Lerner et al. | |
| 2007/0048380 A1 | 3/2007 | Heese et al. | |
| 2007/0232528 A1 | 10/2007 | Franke | |

FOREIGN PATENT DOCUMENTS

| | | |
|---|---|---|
| CA | 2295469 | 7/2000 |
| DE | 3422619 | 12/1985 |
| DE | 19626045 | 1/1998 |
| DE | 19901683 | 7/2000 |
| DE | 19927689 | 12/2000 |
| DE | 69626116 | 10/2003 |
| DE | 10334187 | 3/2005 |
| EP | 0548595 | 6/1993 |
| EP | 0691843 | 2/1997 |
| EP | 1185253 | 3/2002 |
| EP | 1667665 | 6/2006 |
| GB | 1275706 | 5/1972 |
| GB | 1275706 * | 5/1976 |
| JP | 2001 505897 | 11/2005 |
| JP | 4789927 | 6/2007 |
| RU | 2157191 | 3/1994 |
| WO | WO 94/22434 | 10/1994 |
| WO | WO 98/25613 | 6/1998 |
| WO | WO 99/61004 | 12/1999 |
| WO | WO 00/25758 | 5/2000 |
| WO | WO 00/67695 | 11/2000 |
| WO | WO 02/066025 | 8/2002 |
| WO | WO 03/074034 | 9/2003 |
| WO | WO 2004/022633 | 3/2004 |
| WO | WO 2005/023229 | 3/2005 |
| WO | WO 2005/046561 | 5/2005 |
| WO | WO 2005/105055 | 11/2005 |

OTHER PUBLICATIONS

Arzneiformenhehre; "Ein Luhrbuch fur Pharmazeuten;" Wissenschaftliche Verlagsgesellschaft MbH; Stuggart, Germany, pp. 55-56 (1976).

Tschueschow u.a., W.I.; "Industrie Technologie von Arzneimitteln;" Band 2, Charkow, NFAU, MTK-Kniga, pp. 304-305 (2002).

Arzneiformenhehre; "Ein Luhrbuch fur Pharmazeuten;" Wissenschaftliche Verlagsgesellschaft MbH; Stuggart, Germany, pp. 55-56 (1976), with English translation.

(Continued)

*Primary Examiner* — Blessing M Fubara
(74) *Attorney, Agent, or Firm* — D. Peter Hochberg; Sean F. Mellino; Richard A. Wolf

(57) ABSTRACT

A pharmaceutical preparation consisting of various microtablets containing ingredients. The microtablets have the same form and the same weight.

10 Claims, No Drawings

(56) References Cited

OTHER PUBLICATIONS

Tschueschow u.a., W.I.; "Industrie Technologie von Arzneimitteln;" Band 2, Charkow, NFAU, MTK-Kniga, pp. 304-305 (2002), with English translation.

Europat gemassdes Ubereinkommens uber die Ausarbeitung eines Europaischen Arzneibuches, "Europaisches Arzneibuch", with English translation, 1978.

Entmischungsprobleme im Griff, Austragsysteme fur Schuttguter, Chernietechnik, 2001, No. 3 (2001), with English translation.

Schoffling; "Arnzeiformenlehre;" 4th Edition (2003); Chapter 5.2 "Granulate"; Deutscher Apotheker Verlag, pp. 183-183.

Sucker, et al.; "Pharmazeutische Technologie;" Edition 2 (1991); Georg Thieme Verlag, pp. 54-55.

Bauer, et al.; "Lehrbuch der Pharmazeutishen Technologie;" Edition 7 (2002); Wissenschaftliche Verlagsgesselschaft, pp. 133-135.

Univ. of Hamburg (1998), pp. 1-5 and 171-177.

Bornhoft; "K-Carrageenan: Ein neuer Pelletierhilfsstoff zur Feuchtextrusion/Spharonisation;" Dissertation, Univ. of Halle-Wittenberg (2005), pp. 16 and 23.

Fahrig, et al.; "Die Kapsel;" Band 7, Wissenschaftliche Verlagsgesellschaft (1983), pp. 104-107.

Nordmark Arzneimittel GmbH & Co. KG; http://www.nordmark-pharma.de/en/products-service/products/-pancreatin-drug-products.html; Aug. 6, 2013.

Lennartz, Peter; "Untersuchungen zu speziellen Eigenschaften und zur inneren Struktur von Minitabletten aus Paracetamol und sprühgetrockneter Laktose," Univ. of Hamburg, 1998, (English summary—pp. 175-177.).

* cited by examiner

MICROTABLET-BASED PHARMACEUTICAL PREPARATION

CROSS-REFERENCE TO RELATED APPLICATIONS

This application is a National Stage application of International Application No. PCT/DE2007/000415, filed on Feb. 9, 2007, which claims priority of German application number 10 2006 006 532.8, filed on Feb. 10, 2006, both of which are incorporated herein by reference in their entireties.

BACKGROUND OF THE INVENTION

1. Field of the Invention

The present invention relates to a novel pharmaceutical preparation which comprises various microtablets with different constituents, the microtablets having the same spatial shape and the same weight.

2. Description of the Prior Art

Microtablets are known, for example, from DE 342 26 19 A1. The specification describes cylindrical shaped bodies having a convex upper side and under-side, the cylinder diameter and height of which are independently of one another in the range of from 1.0 to 2.5 mm and are in a ratio to one another of 1:0.5 to 1.5.

It is known to administer various active compounds pharmaceutically with the aid of microtablets, examples being pantoprazole (DE 696 261 16 T 2), analgesics (DE 199 016 83 B4), alkyl hydrogen fumarates and omeprazole (DE 196 260 45 C2).

The problems of pharmaceutical administration of active compounds are described in WO 00/67695. According to this publication, microtablets are conventionally administered in capsules. A disadvantage here for the patient is the difficult and troublesome individual dosing (WO 00/67695, page 1, lines 19 to 21). The document also states that the use of hard gelatin capsules does not solve this problem, since these capsules cannot be swallowed or can be swallowed only with difficulty by patients (WO 00/67695, page 1, lines 22 to 26). Reliable individual dosing is not possible in practice by removing and dividing up the capsule contents, since the contents of one or more capsules would have to be divided up into the required amount. However, this cannot be done by a patient, or can be done only with great effort (WO 00/67695, page 1, lines 33 to 37).

EP 1 185 253 B1 describes oral administration units with the active compounds tramadol and diclofenac. The two active compounds are contained in the administration unit in subunits each formulated separately [0007].

The subunits in the context of EP 1 185 253 B1 are solid medicament formulations which comprise, in addition to the particular active compound and/or its particular physiologically acceptable salts, the conventional auxiliary additives [0010].

The subunits in the context of EP 1 185 253 B1 can be in multiparticulate form, for example as microtablets [0011].

The oral administration unit described in EP 1 185 253 B1 can be in the form of a sachet, a capsule or a tablet [0023].

SUMMARY OF THE PRESENT INVENTION

The object of the present invention is a novel pharmaceutical preparation with which microtablets can be adjusted according to the requirements of the patient and can easily be administered by the patient.

A pharmaceutical preparation based on microtablets has been found, whereby the pharmaceutical preparation contains various microtablets with different constituents, each microtablet having the same spatial shape and the same weight.

All the microtablets for the pharmaceutical preparations according to the invention have the same density and as a result can be easily dosed and combined to give individual preparations.

The preparations according to the invention are preferably in a flowable form. Due to the various microtablets having the same density, no separation of the various microtablets occurs, so that they can be dosed in a similar manner to a liquid.

The preparations according to the invention can easily be administered by the patient.

DETAILED DESCRIPTION OF THE PRESENT INVENTION

In a preferred embodiment of the present invention, the microtablets are present in the pharmaceutical preparation according to the invention in a homogeneous mixture.

The constituents are largely uniformly distributed in the pharmaceutical preparations according to the invention. As a result of the individual microtablets having the same density, the uniform distribution of the constituents remains constant; no separation of the microtablets in the preparation according to the invention due to a different density can occur.

The constituents of the microtablets can be active compounds, further auxiliary substances and fillers.

In the context of the present invention, different active compounds or active compound combinations are distributed over different microtablets. By this means it is easily possible to vary the active compound content in the individual preparations and to adapt it to the individual requirements of the individual patient.

In this manner, it is possible according to the invention for the preparations to be easily composed individually from microtablets as "units", for example according to the doctor's instructions, and to be brought into a form which is easy to administer. The preparation can also be composed, for example, in the pharmacy using the conventional means available there.

It is of course also possible in the context of the present invention to provide individualized standard preparations.

The preparations according to the invention are most easily provided by weighing the individual types of microtablets for a preparation.

The pharmaceutical preparations according to the invention can be administered easily via a dosing spoon, since due to the uniform distribution of the microtablets, the constituents are also distributed uniformly. It is therefore not necessary to pack the microtablets into capsules.

Possible active compounds for the microtablets are in principle all solid active compounds which can be processed into microtablets.

The active compounds in the context of the present invention include, for example, pharmaceuticals, homoeopathically acting substances, vitamins, minerals, probiotic active compounds, enzymes, food supplements and plant extracts which are known per se.

The following active compounds may be mentioned by way of example:

Vitamins, such as, for example, biotin, cholines, cobalamin (B12), folates, inositol, niacin (B3), PABA (para-aminobenzoic acid), pantothenic acid (B5), pyridoxines (B6), riboflavin (B2), thiamin (B1), tocopherols, tocotrienols, vitamin A, vitamin B, vitamin C, vitamin D, natural vitamin E, synthetic vitamin E and vitamin K. The vitamins can be of synthetic or natural origin and can also be in the encapsulated state.

Minerals, such as, for example, boron, calcium, chlorine, chromium, copper, germanium, iodine, iron, magnesium, manganese, minerals (chelated), minerals (colloidal), minerals (coral), minerals (microencapsulated), minerals (yeast), molybdenum, phosphorus, calcium, selenium, silicon, sodium, vanadium, zinc.

Amino acids, such as, for example, L-alanine, L-arginine, L-carnitine, L-carnosine, L-citrulline, L-cystine, L-glutamine, L-histidine, L-isoleucine, L-leucine, L-lysine, L-methionine, L-ornithine, L-phenylalanine, L-proline, L-serine, L-taurine, L-theanine, L-tyrosine, L-valine.

Food supplements, such as, for example, 5-HTP, acetyl-L-carnitine, alpha-lipoic acid, alpha-carotene, anthocyanidins, arabinogalactan, arabinoxylan, arachidonic acid, astaxanthin, ATP (adenosine triphosphate), bee pollen, bee propolis, berberines, beta-1,3-glucan, beta-1,6-glucan, beta-carotene, bromelain, carotenoids, carrageenan, cartilage (bovine), cartilage (shark), casein, catechins, cellulose, cetyl myristoleate, chitosan, chlorophyll, chondroitin sulfate, citicoline, citrus flavonoids, CLA (conjugated linoleic acid), collagen (bovine), chicken collagen, fish collagen, collagen (porcine), colostrum, CoQ10 (coenzyme Q10), creatine, curcumin, D-mannose, DAG (diacylglycerol) oil, daidzein, DHA (docosahexaenoic acid), DHEA, diindolylmethane, EGCG (epigallocatechin-3 gallate), EPA (eicosapentaenoic acid), essential fatty acids, fiber, fish oil, flavonoids, FOS (fructooligosaccharides), genistein, GLA (gamma-linoleic acid), glucomannan, glucosamine HCL, glucosamine sulfate, glutathione, GPC (glycerophosphocholine), green lipped mussel, gum arabic, gum guar, hesperidin, huperzine, hyaluronic acid, immunoglobulin, indole-3-carbinol, inositol, inulin, IP-6 (inositol hexaphosphate), ipriflavone, isoflavones, isomaltol, lactoferrin, lactose, lanolin, lecithin, lignans, lutein, lutein esters, lycopene, maltitol, melatonin, microcrystalline hydroxypitites, MSM (methylsulfonylmethane), N-acetyl-cysteine, N-acetyl-glucosamine, octacosanol, octopamine, oligomeric proanthocyanidins (OPCs), omega-3 fatty acid, omega-6 EFAs, oyster shell, papain, pearl powder, pectin, pepsin, phosphatidylcholine, phosphatidylserine, phospholipids, plant sterol/stanol esters, policosanol, polyphenols, egg protein, fish protein, rice protein, silk protein, soy protein, whey protein, pyruvate, quercetin, red yeast rice, resveratrol, ribose, royal jelly, rutin, salivarius, SAM-e, sea cucumber, silymarin, soy protein isolate, squalenes, super oxide dismutase, theobromine, velvet antler, vincamine, vinpocetin, whey protein isolate, xanthan, xylitol, zeaxanthin, zein.

Plant extracts, such as, for example, acai, acerola, AFA (aphanizomenon flos aquae), Agaricus blazei, alfalfa, blue-green algae, green algae, alisma, allicin, aloe vera, aloe (cape), amla, Andrographis paniculata, angelica, anise, annatto, apple, arjuna, arnica, artichoke, ashwagandha, Asparagus racemosus, astragalus, atractylodes, avocado oil, bacopa, banaba leaf, barberry, barley grass, basil, Belleric myrobalan, berries, bilberry, bitter melon (karela), bitter orange (Citrus aurantium), black cohosh, blackcurrant seed, black pepper, black walnut, blackberry, bladderwrack, blessed thistle, Canadian bloodroot, blue cohosh, blueberry, boneset, borage, boswellia, broccoli, buchu, bupleurum, giant burdock, butcher's broom, butterbur, calendula, California poppy, camphor, camu camu, canola, canola oil, capsaicin, cardamom, carob bean tree, Cascara sagrada, cassia, castor oil, cat's claw, catnip, catuaba, cayenne pepper, cereal grasses, chamomile, Chanca piedra, chaparral, chastetree (vitex), chickweed, chicory, chlorella, chocolate, cinnamon, citrus plant, clove, club moss, cnidium, cocoa, codonopsis, coix, Coleus forskohlii, coltsfoot, comfrey, coral, cordyceps, corydalis, cramp bark, cranberry, cranberry seed extract, cranberry seed oil, cyperus, damiana, dandelion, devil's claw, dong quai, dulse, echinacea, elderberry, elecampane, eleuthero, emblic, ephedra, essential oils, eucalyptus, eucommia, evening primrose, Evodia rutae carpa (wu zhu yu), eyebright, false unicorn, fennel, fenugreek, feverfew, flaxseed, flaxseed oil, flower pollen, fo-ti, frankincense, fruits, ganoderma, Garcinia cambogia, garlic, gentian, ginger, Ginkgo biloba, American ginseng, oriental ginseng, Canadian goldenseal, gotu kola, grains, grape seed extract, grape skin extract, grapefruit seed extract, grapes, graviola, green foods, guacatonga, guarana, guggul, Gymnema sylvestre, hawthron, hemp, hibiscus, honey, honey bush, Hoodia gordonii, hops, horehound, horny goat weed (epimedium), horse chestnut, horsetail, hyssop, Indian long pepper, Irish moss, jiaogulan, jojoba, juniper, kava, kelp, kola nut, kudzu, kukui nut, lavender, lemon balm, lemon grass, liquorice, lobelia, luo han guo, mace, magnolia, maitake, mangosteen, manuka, marshmallow, meadowsweet, melilotus officinalis, milk thistle, motherwort, Mucuna pruriens, Muira puama, mullein, muscadine, therapeutic mushrooms, mustard, myrrh, nattokinase, neem, nettle, noni, cactus, nori, nuts, oat bran, oats, oatstraw, olive, olive leaf, olive oil, oregano, oregon grape, papaya, parsley, passion flower, pau d'arco, peony, peppermint, perilla, perilla seed oil, periwinkle, pine bark extract, plantain, pleurisy, Polygonum cuspidatum, pomegranate, poria, prickly ash, psyllium, pumpkin seed, pumpkin seed oil, pygeum, raspberry, raspberry leaf, red clover, red raspberry seed oil, rehmannia, reishi, rhodiola, rhubarb, rice bran, rooibos, rose hips, rosemary, safflower, safflower oil, sage, salvia root, sandalwood, sangre de grado, sarsaparilla, saw palmetto, schizandra, sea buckthorn, seaweed, seed, senna leaves, sesame oil, sesame seed, shea, sheperd's purse, shiitake, silymarin, skullcap, slippery elm, soy, soy oil, spearmint, spirulina, sprouts, squaw vine, St. John's wort, stevia, strawberry, suma, sunflower oil, sunflower seed, tamanu oil, tea tree, black tea, green tea, thyme, tomato fiber, tongkat ali, Tribulus terrestris, triphala, tulsi (holy basil), turmeric, Uva ursi, valerian, vanilla, vegetables, vervain, vinca minor, vinegar, Wasabia japonica, wheat germ, wheat grass, white kidney bean, white willow bark, wild cherry, wild yam, witch hazel, wolfberry (lycium), wormwood, yacon, yarrow, yeast, yellow dock, Yerba mate, Yerba santa, ylang ylang, yohimbe, yucca, zizyphus.

The microtablets of a preparation in the context of the present invention must all have the same weight and the same spatial shape. The weight is adjusted according to the choice of active compounds by varying the fillers.

In the case of other preparations, microtablets having a different weight and another spatial shape can of course be employed.

The weight of an individual microtablet depends on the composition and, where appropriate, on the coating. By changing the contents of the auxiliary substances and fillers, microtablets which have different active compounds and the same weight can be achieved.

The surface of the microtablets can be coated in a manner known in the art. By this, for example, administration can be facilitated or the active compound can be protected (e.g. from gastric acid).

The spatial shape of the microtablets can in principle be chosen as desired. However, the spatial shape should be such that there is no hindrance from the individual microtablets during homogenization.

The microtablets in the context of the present invention preferably have a cylindrical, elliptical or spherical spatial shape.

The size of the microtablets in cylindrical shape in the context of the present invention can in general have a height and a diameter of from in each case about 1 to about 4 mm, preferably from 1 to 2.5 mm.

For example, a microtablet in a cylindrical shape with a height and a diameter of about 2 mm each can have a weight of from 6.5 to 8.5 mg.

The microtablets in the context of the preparations according to the invention are very accurately worked and allow only very minor deviations in the context of international pharmacopoeias.

The preparation of the microtablets in the context of the preparations according to the invention is known in the art.

The homogenization (i.e. the uniform distribution) of the microtablets in a preparation according to the invention can be carried out by processes known in the art. The microtablets are not destroyed during this.

A process has also been found for the preparation of pharmaceutical preparations based on microtablets with different constituents, whereby microtablets having the same spatial shape and the same weight are mixed homogeneously.

The preparations prepared according to the invention can be stored in a bottle in a stable manner for a long period of time, and during the administration can be filled from the bottle into a measuring vessel. The composition of the recipe and the flowability are retained here.

The present invention also provides the use of the preparations according to the invention which contain various microtablets with different constituents, each microtablet having the same spatial shape and the same weight, for treatment and prevention of diseases.

The preparations according to the invention can be easily prepared in an advantageous manner and easily administered in an individualized form. They extend in a novel manner the administration possibilities of agents for treatment and prevention of diseases.

EXAMPLE

Preparation for a diabetic for treatment of the disease symptoms. There are the following four types
  Bio-fruits n Greens 2,000 mg per day×30 days=60 grams—antioxidants
  Bio-Glucoban 350 mg per day×30=10.5 grams—combination of 4 extracts (Mormodica charantia, Legerstroemia speciosa, Centella asiatica and alpha-lipoic acid), which as phytoinsulin have the effect of improving the circulation for better transportation of glucose into the cells and for reducing insulin resistance.
  Bio-Eye Health 250 mg per day×30=7.5 grams—combination of carotenoids, lutein, astanxathin, if vision is already impaired.
  Bio-CardioHealth—500 mg per day×30=15 grams—combination of natural tocotrienols and tocopherols (full spectrum vitamin E), natural vitamin C and coenzyme Q10.

Each microtablet has 5 mg as the active substance and has a weight of 7.5 mg including the additives.

The dosages depend on the weight and clinical picture of the patient.

The microtablets are cylindrical and have a height of 2 mm and a diameter of 2 mm.

According to the predetermined dosage, the four different types of microtablets are homogenized in a shaking beaker and can be removed with a measuring vessel. The preparation is readily flowable.

What has been described above are preferred aspects of the present invention. It is of course not possible to describe every conceivable combination of components or methodologies for purposes of describing the present invention, but one of ordinary skill in the art will recognize that many further combinations and permutations of the present invention are possible. Accordingly, the present invention is intended to embrace all such alterations, combinations, modifications, and variations that fall within the spirit and scope of the appended claims.

The invention claimed is:

1. A flowable pharmaceutical preparation comprising a homogenous mixture of various groups of microtablets, wherein each microtablet has a different composition, and wherein the composition comprises at least one active compound selected from the group consisting of vitamins, minerals, amino acids, food supplements and plant extracts, and further comprises fillers, each microtablet having the same spatial shape, the same weight and the same density, wherein the microtablets will not separate, wherein said preparation is not a capsule, and wherein said microtablets comprise a height in the range of from 1 to 3 mm and a diameter in the range of from 1 to 3 mm.

2. The pharmaceutical preparation according to claim 1, wherein said homogenous mixture of microtablets comprises a uniform distribution of said microtablets, and wherein said pharmaceutical preparation is administrable while maintaining the uniform distribution of the microtablets.

3. The pharmaceutical preparation as claimed according to claim 1, wherein the microtablets have a spatial shape selected from the group consisting of a cylindrical shape, an elliptical shape and a spherical shape.

4. The pharmaceutical preparation according to claim 1, wherein the microtablets have a weight in the range of from 4 to 8 mg.

5. The pharmaceutical preparation according to claim 1, wherein the microtablets have a spatial shape selected from the group consisting of cylindrical, elliptical and spherical.

6. The pharmaceutical preparation according to claim 5, wherein the microtablets comprise a cylindrical shape and comprise a height and a diameter in the range of from about 1 to about 3 mm.

7. The pharmaceutical preparation according to claim 6, wherein the microtablets comprise a cylindrical shape and comprise a height and a diameter in the range of from about 1 to 2.5 mm.

8. The pharmaceutical preparation according to claim 7, wherein the microtablets comprise a cylindrical shape, comprise a height and a diameter of about 2 mm and a weight in the range of about 6.5 to 8.5 mg.

9. A process for preparing flowable pharmaceutical preparations comprising a homogenous mixture of various groups of microtablets, with each microtablet having a different composition, wherein the composition comprises at least one active compound selected from the group consisting of vitamins, minerals, amino acids, food supplements and plant extracts, and further comprises fillers, each microtablet having the same spatial shape, the same weight and the same density, wherein the microtablets will not separate, wherein said preparation is not a capsule and wherein said microtablets comprise a height in the range of from 1 to 3 mm and a diameter in the range of from 1 to 3 mm, said process comprising the steps of homogenously mixing said microtablets having the same spatial shape, the same density and the same weight in a shaking beaker, and removing the microtablets with a measuring vessel to obtain said flowable preparation.

10. A method for preparing a flowable pharmaceutical preparation comprising a homogenous mixture of various groups of microtablets, with each microtablet having a different composition, wherein the composition comprises at least one active compound selected from the group consisting of vitamins, minerals, amino acids, food supplements and plant extracts, and further comprises fillers, each microtablet having the same spatial shape, the same weight and the same density, wherein said microtablets will not separate, wherein said preparation is not a capsule, and wherein said microtablets comprise a height in the range of from 1 to 3 mm and a diameter in the range of from 1 to 3 mm, said method comprising the step of homogenously mixing said microtablets having the same spatial shape, the same density and the same weight in a mixing beaker.

\* \* \* \* \*